United States Patent [19]

Darragh et al.

[11] 4,073,787
[45] Feb. 14, 1978

[54] MANUFACTURE OF PYRIDINE AND METHYLPYRIDINES

[75] Inventors: John Irvine Darragh, Runcorn; Hugh Stewart Inglis, Stockton-on-Tees, both of England

[73] Assignee: Imperial Chemical Industries Limited, United Kingdom

[21] Appl. No.: 760,145

[22] Filed: Jan. 17, 1977

[30] Foreign Application Priority Data

Jan. 30, 1976 United Kingdom .................. 3789/76

[51] Int. Cl.$^2$ .......................................... C07D 213/12
[52] U.S. Cl. ................................................ 260/290 P
[58] Field of Search ..................................... 260/290 P

[56] References Cited

U.S. PATENT DOCUMENTS

| | | | |
|---|---|---|---|
| 2,549,651 | 4/1951 | Weisgerber | 260/290 P |
| 3,575,986 | 4/1971 | Crist et al. | 260/290 P |

*Primary Examiner*—Alan L. Rotman
*Attorney, Agent, or Firm*—Cushman, Darby & Cushman

[57] ABSTRACT

The present invention involves the manufacture of pyridine and/or methylpyridines, which comprises the catalytic vapor phase reaction of 1,3-butadiene, formaldehyde and ammonia in the presence of a gaseous diluent such as steam.

5 Claims, No Drawings

MANUFACTURE OF PYRIDINE AND METHYLPYRIDINES

This invention relates to the manufacture of pyridine and methylpyridines.

According to the present invention there is provided a process for the manufacture of pyridine and/or methylpyridines which comprises the catalytic vapour-phase reaction of 1,3-butadiene, formaldehyde and ammonia.

Suitable catalysts for use in the process of the present invention include those known as catalysts for the vapour-phase reaction between formaldehyde, acetaldehyde and ammonia, for example the dehydration and/or cracking catalysts described in the specification of UK Pat. No. 1,070,664.

It is preferred to use a catalyst comprising silica-alumina.

The catalyst may be employed either as a fixed bed or in the form of a fluidised bed.

The reaction may be carried out over a wide range of temperature, for example from 300° C to 550° C but the preferred temperatures are those in the range 300° C to 400° C.

The reaction is preferably carried out at substantially atmospheric pressure but higher or lower pressures may be used.

The molar ratio of ammonia to total formaldehyde and butadiene is preferably at least 0.5 to 1; it is especially preferred to use at least 1 mole of ammonia per mole of total formaldehyde and butadiene, for example from 1 to 5 moles of ammonia per mole of total formaldehyde and butadiene.

The relative proportions of formaldehyde and butadiene may vary widely but the reaction mixture preferably contains at least 0.2 mole of formaldehyde per mole of butadiene (for example from 0.5 to 3 moles of formaldehyde per mole of butadiene).

Formaldehyde may be introduced as such or in the form of a compound giving rise thereto under reaction conditions. Thus, for example trioxane, methanol or methylal may be used as sources of formaldehyde.

The reaction is preferably carried out in the presence of nitrogen and/or another gaseous diluent (for example steam).

The proportion of pyridine (relative to methylpyridines) in the product is in general increased by the incorporation of molecular oxygen in the reaction mixture.

It is preferred to carry out the reaction in the presence of steam, for example at least 3 moles of steam for each total mole of formaldehyde and butadiene. While the proportion of steam may be considerably in excess of this ratio an upper limit will, in practice, be imposed by the desirability of maintaining an acceptably high throughput of the reactants. Thus while the proportion of steam may be, for example, from 3 to 20 moles of steam per total mole of formaldehyde and butadiene there is in general little to be gained by using more than about 10 moles of steam per total mole of formaldehyde and butadiene.

Whether oxygen is added, and if so in what proportion, will depend upon whether it is desired to optimise the direct conversion into pyridine or whether it is preferred to optimise the conversion into total pyridine bases (including methylpyridines).

Even when pyridine itself is the product mainly desired it may sometimes be advantageous to optimise the conversion into total pyridine bases and subsequently subject the methylpyridines to demethylation. The reaction products may conveniently be passed directly to a dealkylation process without an intermediate separation stage. Thus the reaction products (including pyridine and methylpyridines) may be maintained in the vapour phase and passed continuously to a stage wherein methylpyridines are demethylated in the presence of a dealkylation catalyst, which may be the same as, or different from, the catalyst employed in the stage of the primary reaction between formaldehyde, butadiene and ammonia.

If desired, steam or further steam may be introduced at the demethylation stage (or between the primary stage and the demethylation stage). Molecular oxygen may also be introduced at the demethylation stage (or between the primary stage and the demethylation stage).

Pyridine and/or methylpyridines may be separated from the reaction products by known methods, for example by distillation, extraction or a combination of such methods.

The invention is illustrated by the following Examples.

EXAMPLE 1

A gaseous mixture of 1,3-butadiene (1.7% by volume), formaldehyde (1.6% by volume), ammonia (8.1% by volume), air (32.5% by volume), steam (31.7% by volume) and nitrogen (24.4% by volume) was passed through a fluidized bed of silica-alumina catalyst, commercially available as "Synclyst" (Trade Mark) - grade 3A MS/13/HD, maintained at 320° C. The contact time was 5 seconds and the mixture was passed for a period of 5 hours during which time 0.41 mole of 1,3-butadiene and 0.38 mole of formaldehyde were fed. The gases from the reaction zone were cooled to give a liquid product containing pyridine bases. The uncondensed gases were scrubbed with water to recover a further quantity of pyridine bases. The residual off-gases contained 0.326 mole of unreacted 1,3-butadiene corresponding to a molar conversion of 20.7%. 0.03 mole of pyridine, 0.0037 mole of 3-methylpyridine and 0.0006 mole of 2- and 4-methylpyridines were produced, corresponding to 35% molar yield of pyridine on butadiene consumed.

EXAMPLE 2

Following the same general procedure as in Example 1, a gaseous mixture of 1,3-butadiene (2.1% by volume), formaldehyde (1.7% by volume), ammonia (7.8% by volume), air 31.5% by volume), steam (33.2% by volume) and nitrogen (23.7% by volume) was passed through a fluidised bed of "Synclyst" catalyst (previously treated with fluosilicic acid in an amount corresponding to 5% by weight of the catalyst) maintained at 320° C. The contact time was 4.9 seconds and the mixture was passed over a period of 4 hours during which time 0.41 mole of 1,3-butadiene and 0.33 mole of formaldehyde were fed. 0.352 mole of unreacted butadiene was recovered corresponding to a molar conversion of 14.8%. A total of 0.027 mole of pyridine and 0.0055 mole of 3-methylpyridine were formed, corresponding to a pyridine yield of 44% of the butadiene consumed.

EXAMPLE 3

A gaseous mixture containing 1,3-butadiene (2.0% by volume), formaldehyde (1.6% by volume), ammonia (8.1% by volume), steam (31.6% by volume) and nitrogen (56.7% by volume) was passed through a fluidised "Synclyst" catalyst at 350° C. The contact time was 5 seconds and the mixture was passed for 4 hours, during which time 0.39 mole of 1,3-butadiene and 0.31 mole of formaldehyde were fed. The molar conversion of butadiene was 22.6%. A total of 0.008 mole of pyridine and 0.014 mole of 3-methylpyridine was produced, corresponding to a yield of pyridine of 9% (based on butadiene consumed).

The total yield of pyridine bases (on grams carbon consumed) was 19%.

What is claimed is:

1. A process for the manufacture of pyridine which comprises the vapor-phase reaction, in the presence of a catalyst comprising silica-alumina and at a temperature in the range from 300° C to 550° C, of 1,3-butadiene, formaldehyde and ammonia in the presence of a gaseous diluent comprising steam wherein the proportions of the reactants are at least 0.5 mole of ammonia per total mole of formaldehyde and butadiene and at least 0.2 mole of formaldehyde per mole of butadiene and wherein the proportion of steam is at least 3 moles of steam per total mole of formaldehyde and butadiene.

2. A process as set forth in claim 1 in which there is also produced a methylpyridine.

3. A process according to claim 1 wherein the reaction is carried out at a temperature in the range from 300° C to 400° C.

4. A process according to claim 1 wherein at least 1 mole of ammonia is employed per total mole of formaldehyde and butadiene.

5. A process according to claim 1 wherein the reaction mixture comprises molecular oxygen.

* * * * *